United States Patent
Schnell et al.

[19]

[11] Patent Number: 6,071,269
[45] Date of Patent: Jun. 6, 2000

[54] BLOOD SET AND CHAMBER

[75] Inventors: William J. Schnell, Libertyville, Ill.;
David S. Utterberg, Seattle, Wash.

[73] Assignee: Medisystems Technology Corporation, Las Vegas, Nev.

[21] Appl. No.: 09/078,020

[22] Filed: May 13, 1998

[51] Int. Cl.⁷ .............................. A61B 19/00; A61M 5/00
[52] U.S. Cl. ................. 604/406; 604/251; 604/4
[58] Field of Search ................... 604/403, 405, 604/406, 4–6, 65, 67, 80–83, 245, 246, 251, 254

[56] References Cited

U.S. PATENT DOCUMENTS

| | | | |
|---|---|---|---|
| 4,191,182 | 3/1980 | Popovich et al. | 128/214 R |
| 4,200,095 | 4/1980 | Reti | 128/214 C |
| 4,486,188 | 12/1984 | Altshuler et al. | 604/4 |
| 4,512,163 | 4/1985 | Wells et al. | 128/400 |
| 4,583,981 | 4/1986 | Urquhart et al. . | |
| 4,941,875 | 7/1990 | Brennan | 604/81 |
| 4,946,439 | 8/1990 | Eggers | 604/67 |
| 5,059,173 | 10/1991 | Sacco | 604/80 |
| 5,368,555 | 11/1994 | Sussman et al. | 604/4 |
| 5,578,070 | 11/1996 | Utterberg . | |
| 5,643,250 | 7/1997 | Utterberg . | |
| 5,681,294 | 10/1997 | Osborne et al. | 604/251 |
| 5,730,730 | 3/1998 | Darling, Jr. | 604/246 |
| 5,830,185 | 11/1998 | Block, Jr. . | |

FOREIGN PATENT DOCUMENTS

WO 98/23353  6/1998  WIPO .

OTHER PUBLICATIONS

One page printed sheet entitled: Medisystems D3–9600/9700 ReadySet™ Bloodtubing, Issue Date Mar. 1993.

*Primary Examiner*—Corrine McDermott
*Assistant Examiner*—David J. Cho
*Attorney, Agent, or Firm*—Gerstman, Ellis & McMillin, Ltd.

[57] ABSTRACT

A combined arterial-venous blood flow set comprises connected lengths of flexible tubing for receiving blood from a patient, for conveying the blood to a blood processing device such as a dialyzer or an LDL filter, and for returning the blood to the patient. An optional first bubble trap chamber is connected in series flow between two of the lengths of tubing at a flow position downstream from the patient and upstream from the blood processing device. A second bubble trap chamber is connected in series flow between two of the lengths of tubing at a flow position downstream from the blood processing device and upstream from the patient. A first portion of the tubing which is in a flow position upstream from the blood processing device extends by the second bubble trap chamber, and is physically, laterally connected to it without direct flow connection. This helps to stabilize the positioning of components of the flow set and to reduce confusion in set-up and priming.

12 Claims, 2 Drawing Sheets

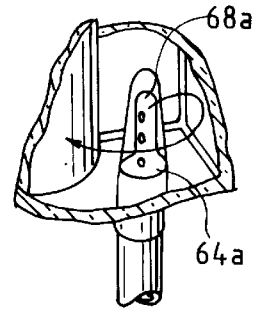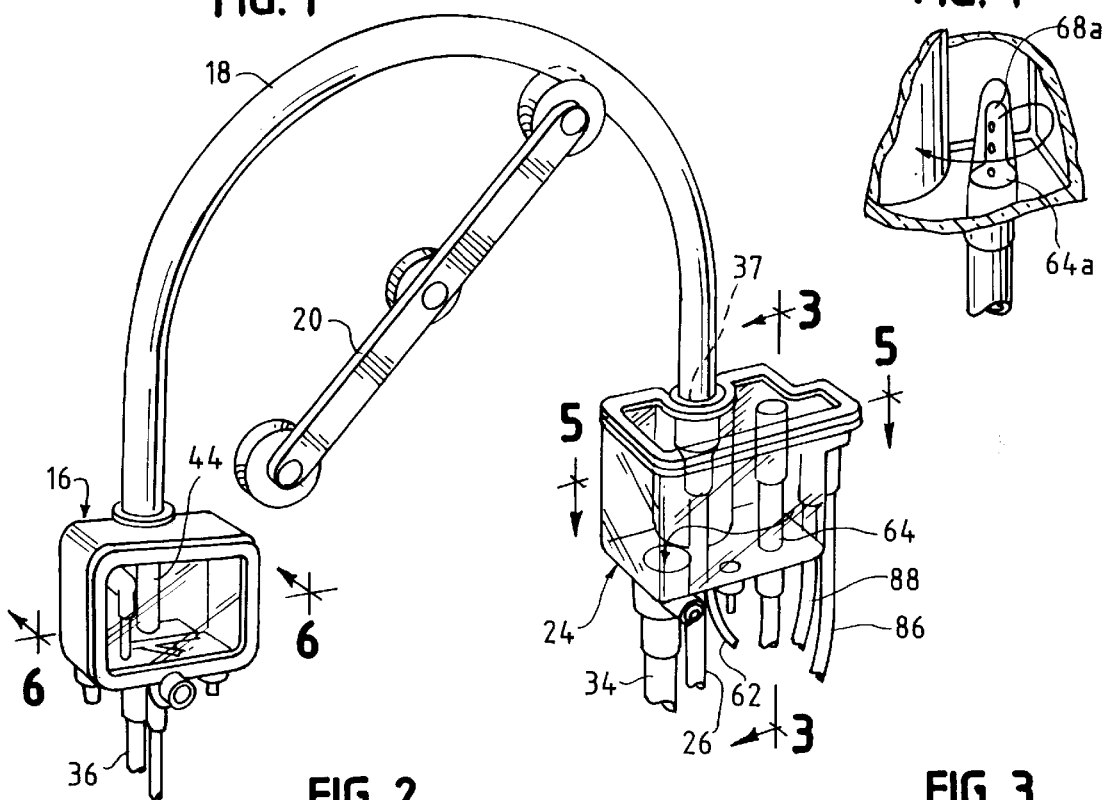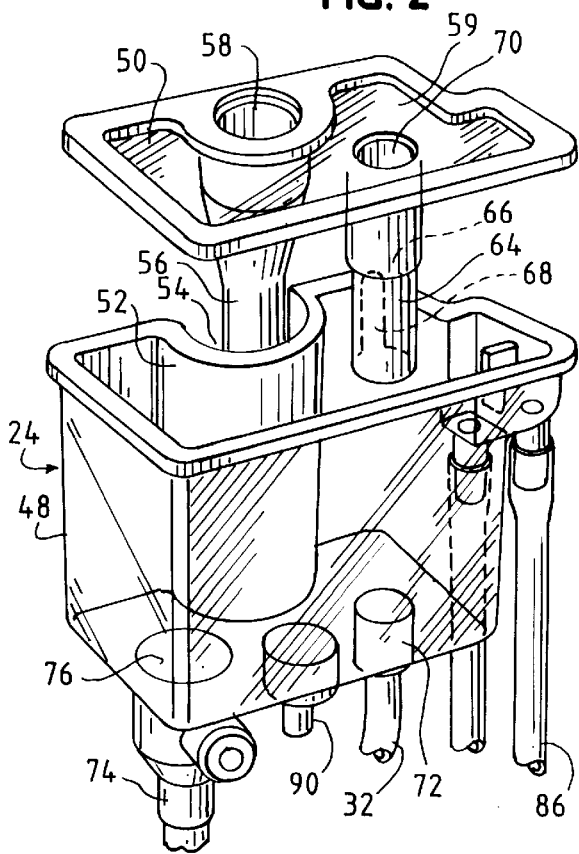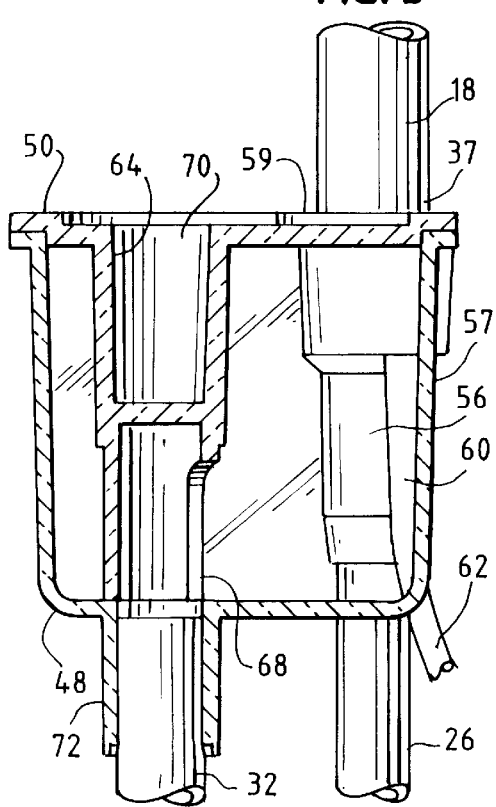

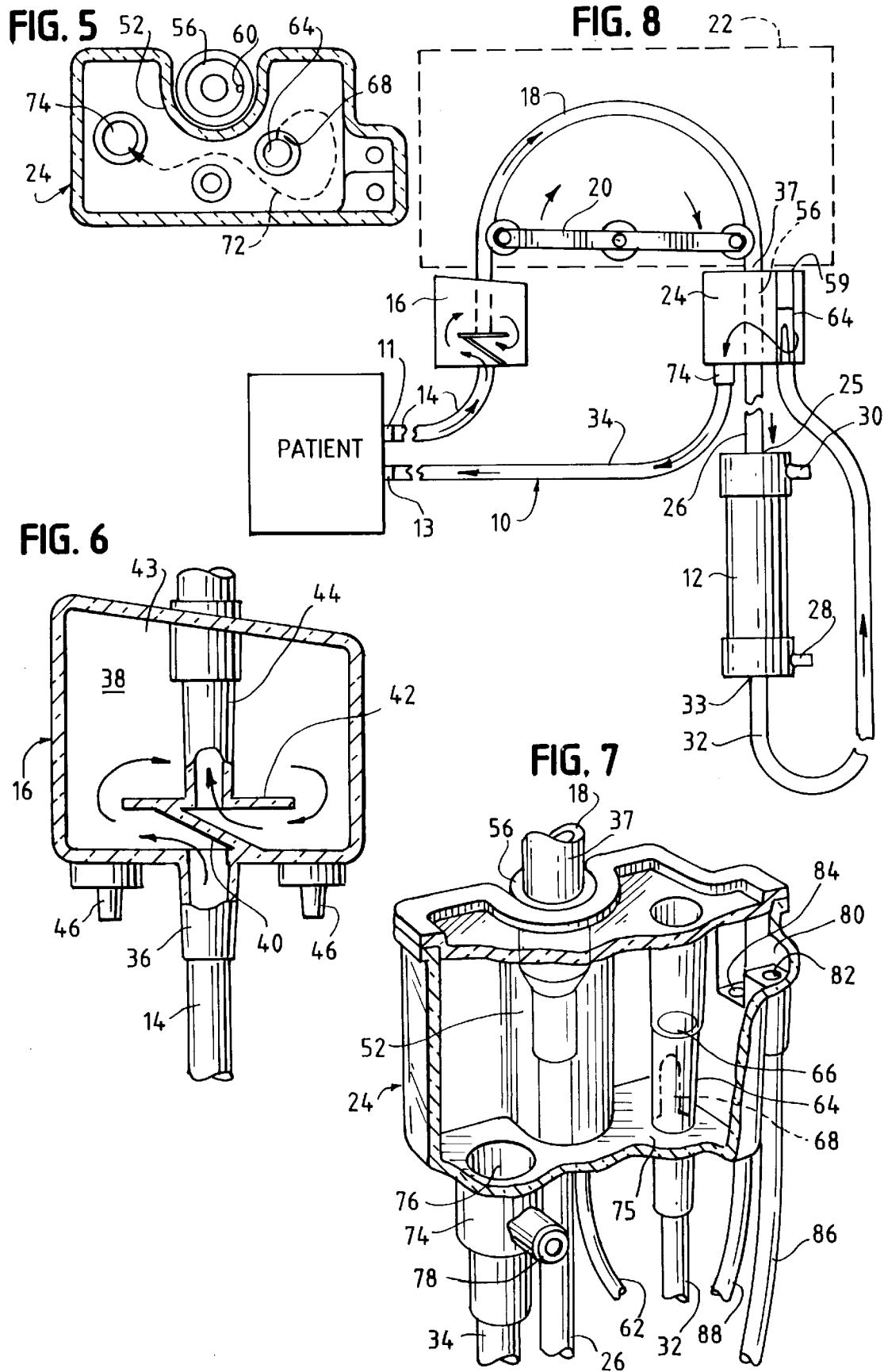

BLOOD SET AND CHAMBER

BACKGROUND OF THE INVENTION

Blood sets are used for conveying blood between a patient and an extracorporeal blood treatment device such as a dialyzer. Typically, an extracorporeal blood treatment system uses two separate blood sets: an arterial blood set and a venous blood set for respectively conveying blood from the patient to the treatment device, and for conveying blood from the treatment device back to the patient. Accordingly, an extracorporeal blood treatment system such as a hemodialysis system generally has a complex series of tubes and other set components such as bubble trap chambers, peristaltic pump tubing, branch connectors, and the like. The handling and set up of such blood sets with a device such as a hemodialyzer is complex and confusing.

By this invention, the handling of extracorporeal blood treatment sets can be simplified, with greater flexibility of use because the same sets can be used with different designs of commercially available dialysis machines. Particularly, by this invention it becomes practical to provide a flexible tubing blood set that is both an arterial set and a venous set, for the simplification of installation and priming, and also for a possible reduction in the number of connections that must be made, and reduction in cost and overall complexity. Also, new designs of blood chambers are used herein.

DESCRIPTION OF THE INVENTION

By this invention, a combined arterial-venous blood flow set may be provided for extracorporeal blood treatment, which sets may fit a plurality of existing dialysis machines. The set comprises connected lengths of flexible tubing for receiving blood from the patient, for conveying the blood to a blood processing device such as a dialyzer, and for returning the blood to the patient.

The blood flow set of this invention comprises an optional first bubble trap chamber which is connected in series flow between two of the lengths of tubing at an arterial flow position, namely a flow position which is downstream from the patient but upstream from the blood processing device.

A second bubble trap chamber may be connected in series flow between two of the lengths of tubing at a venous flow position, which is downstream from the blood processing device and upstream from the patient, so that blood may be circulated through the extracorporeal system from the patient and then returned to the patient.

A first portion of the tubing, which is in a flow position upstream from the blood processing device, extends by the second bubble trap chamber. This first portion of tubing is physically connected to the bubble trap chamber without flow connection with the bubble trap chamber. This helps to stabilize the positioning of components of the flow set.

Particularly, one of the lengths of tubing may comprise peristaltic pump tubing. Preferably, the first bubble trap chamber is directly connected in flow communication to an end of the pump tubing. The second bubble trap chamber may be externally connected to tubing adjacent the pump tubing (including the possibility of being directly externally connected to the pump tubing), but this second chamber is out of direct flow communication therewith. Instead, the pump tubing adjacent to the second bubble trap chamber, and connected tubing, may comprise the first portion of the tubing as described above which is physically connected to the second bubble trap chamber without direct flow connection. Blood from the pump tubing passes externally by the second bubble trap chamber to the dialyzer or other blood treatment device. Then, the blood is returned to the second bubble trap chamber for final debubbling before being returned to the patient.

This arrangement provides a significant improvement in the ease of installation of the arterial and venous set into, particularly, conventional commercial hemodialysis machines or other blood treatment devices, such as low density lipid (LDL) removing systems. As the peristaltic pump tubing is installed into the peristaltic pump housing, the two bubble trap chambers which are preferably present are positioned in known positions adjacent to the pump housing, causing a known positioning of the various chambers and tubing sections, for connection to the dialyzer and to the patient with greater ease than is found with the separate installation and connection of separate arterial sets and venous sets. Specifically, the bottom of the pump housing of the dialysis machine can help to position the set chambers as the set is installed, avoiding the need for extra tube retention clips.

The second bubble trap chamber is also novel in itself, comprising a chamber-defining housing, plus a flow inlet tube connected to a length of the flexible tubing which is in a flow position downstream from the blood processing device (typically a dialyzer). The flow inlet tube extends into the chamber adjacent to one side of the chamber, and has an aperture that directs substantially the entire flow of blood through the inlet tube horizontally into the chamber. The housing also has an outlet port which is positioned adjacent to the chamber bottom, and is further positioned adjacent to an opposed side of the chamber to the one side.

The chamber has a sidewall that defines a flow-diverting indentation positioned between the one side and the opposed side of the chamber. The effect of this flow diverting indentation is to interfere with a direct flow path of blood flowing through the chamber between the flow inlet tube and the outlet port. Thus, a substantial portion of the blood entering the chamber, typically most of the blood, follows a circuitous path around the peripheral wall of the chamber in travelling from the flow inlet tube to the outlet port. This longer flow path gives bubbles in the blood more time to rise to the surface of the chamber, keeping away from the outlet port, which is positioned adjacent to the chamber bottom. Thus, a smaller bubble trap can be used having a longer flow path and equal or better bubble removing effect than larger bubble traps of different designs. This provides the advantage that the blood chamber of this invention may have less volume, which means that less blood is maintained outside of the patient during the blood handling process.

Preferably, the aperture of the flow inlet tube faces away from the outlet port by at least about 90°, to facilitate this longer, circuitous blood flow path through the bubble trap chamber.

Typically, the first portion of tubing, referred to above, is externally connected to the second bubble trap chamber at a position to permit the fluid flow of the first portion of tubing to pass through a recess defined by the outside surface of the portion of the second bubble trap chamber sidewall that defines the indentation. Thus, the recess-defining side of the bubble trap chamber can be rather flat, and can stably rest against a flat surface of dialyzer hardware during use, while providing the external blood flow passageway adjacent to the side and in the recess as described above. The chamber top can also be substantially flat, to allow it to stably rest against the underside of a commercial dialysis machine pump housing. This facilitates the use of the chamber and set of this invention with a variety of conventionally available dialysis machine hardware, for which the combined arterial-venous set of this invention comprises a removable, and often disposable, component along with the membrane dialyzer unit or other blood processing device such as an LDL filter.

Specifically, the housing of the second bubble trap chamber carries an integral tube extending through the above described recess, with the integral tube having opposed ends which may be connected to separate lengths of the flexible tubing of the set, to define the first portion of the tubing.

The housing of the second bubble trap chamber may define a cup-like main body which, in turn, defines a bottom wall and sidewall. Also, the housing comprises a fitting lid which is sealed to an open mouth of the main body. The fitting lid thus defines a closed chamber with the main body. Also, the lid may define and carry the integral tube which extends through the recess as described above.

The sidewall of the second bubble trap chamber also may define at least one side chamber that is vertically spaced from the bottom of the bubble trap. A side chamber has at least one port that connects to tubing located externally of the second bubble trap chamber. Thus, the level of liquid in the second bubble trap chamber may be controlled through these one or more side chambers. The second bubble trap chamber may have a substantially flat lid so that it can rest essentially flush underneath a projecting ledge of a roller pump housing, to fit with present commercial designs of dialysis machine hardware.

A blood filter may be carried in or adjacent to the outlet port of the second bubble trap chamber, to filter blood passing through the outlet port.

The first bubble trap chamber may also have a flow inlet that directs flowing blood horizontally into the first chamber. The first bubble trap chamber may be of a design as disclosed in Schnell and Utterberg U.S. patent application Ser. No. 08/905,245, filed Aug. 1, 1997.

Particularly, the first bubble trap chamber may comprise a chamber having top, bottom, and side walls. Typically, the chamber defines a substantially flat, lateral side. A first port tube communicates upwardly into the chamber, while a second port tube communicates downwardly into the chamber, preferably in coaxial relationship with the first port tube. A flow directing system is positioned to direct incoming fluid from one of the port tubes into a first lateral flow direction, and then to allow substantially horizontal fluid flow circulation in the chamber. The flow-directing system also allows fluid flow from circulating fluid in the chamber into the other of the port tubes in a lateral flow direction that typically is generally the same as the first lateral flow direction, while preventing direct flow between the first and second port tubes.

Additionally, this invention relates to sets of differing designs which carry the second bubble trap chamber as described above, optionally without the presence of chambers of the design of the first bubble trap chamber. Such sets may conventionally contain peristaltic pump tubing, branch connector lines, other designs of bubble removing chambers, filters, and the like as and if desired.

DESCRIPTION OF THE DRAWINGS

In the drawings,

FIG. 1 is a perspective view of a portion of a combined arterial-venous blood flow set showing the first and second bubble trap chambers;

FIG. 2 is an enlarged, exploded, perspective view of the second bubble trap chamber as shown in FIG. 1;

FIG. 3 is a sectional view taken along line 3—3 of FIG. 1;

FIG. 4 is a fragmentary, perspective view showing a variation of the inlet tube of the second bubble trap chamber;

FIG. 5 is a sectional view taken along line 5—5 of FIG. 1;

FIG. 6 is an enlarged, longitudinal sectional view of the first bubble trap chamber, also shown in FIG. 1;

FIG. 7 is an enlarged, perspective view, with portions broken away, of the second bubble trap chamber of FIG. 1; and FIG. 8 is a partially schematic diagram showing the overall flow pattern of the combined arterial-venous set of this invention, depicted with shortened flow tubings for simplicity of disclosure.

DESCRIPTION OF SPECIFIC EMBODIMENTS

Referring to the drawings, FIG. 8 shows an overall, partially schematic view of the combined arterial-venous set 10 of this invention, and the blood flow path between the patient and a conventional dialyzer 12.

The blood access to a patient may be performed in a conventional manner with conventional fistula needle connectors 11, 13, for example by connection with a fistula on the patient's arm or an implanted hemodialysis catheter in a vein. Blood flows from the patient through a first length of flexible tubing 14. The blood flows from first length of tubing 14 into first bubble trap chamber 16. From there, the blood flows through connected peristaltic or roller pump tubing 18, shown to be installed in a peristaltic pump component 20 of a conventional dialysis machine 22.

The blood is pumped through tubing 18, and then through a joined conduit 56, which is connected to second bubble trap chamber 24 but, in accordance with this invention, the blood does not communicate with the interior of chamber 24, but merely passes through conduit 56, which is externally secured to chamber 24. A third length of flexible tubing 26 joins with connector tube conduit 56, and extends from second bubble trap chamber 24 to the blood inlet 25 of a conventional, hollow fiber hemodialyzer 12, where the blood is dialyzed against dialysis solution which enters the dialysis system through side inlet 28 and exits via side outlet 30. It should be added that dialyzer 12 may be inverted, with the blood coming in through the bottom thereof if desired, and the dialysis solution entering at the top, this being accompanied by appropriate lengthening and placement of the flexible tubing of set 10.

The arterial portion of the blood flow path ends at dialyzer 12. The venous portion of the flow path begins at fourth section of flexible tubing 32, which extends downstream from the blood outlet 33 of dialyzer 12 into flow communication with the interior of second chamber 24 through inlet tube 64. Flowing blood passes through chamber 24 and out therefrom through outlet port 74 into fifth length of flexible tubing 34. This length of flexible tubing then communicates back to the patient, so that the blood is returned.

The combined arterial-venous blood flow set as shown in FIG. 8 lacks branch lines, injection sites, and other components that would be actually found in such a set used for blood dialysis or another extracorporeal blood processing procedure. These components may be added to the basic set as shown in an appropriate manner corresponding to medical need and the known configurations of such blood sets. The sets of this invention may be similar to conventional sets, except as otherwise described herein.

By this invention, the combined arterial-venous set is held together and simplified by the external connection of the first portion of tubing comprising in this embodiment a downstream portion 37 of pump tubing 18 and an upstream portion of third length of flexible tubing 26, which are respectively secured to connector tube conduit 56 of second bubble trap chamber 24. Thus, the first portion of tubing, which is part of the arterial system of the set, is externally secured to second chamber 24, which is part of the venous system. This tends to hold the set together in a more understandable way so that a novice attempting to mount the set into hemodialyzer hardware 22 is not confused and delayed by the typical mass of tubing, sometimes called "spaghetti", including branch tubing and the like.

The basic architecture of the set up thus becomes very easy. The user simply takes the set comprising trap chambers 16, 24, with pump tubing 18 between them, and installs it in the roller pump assembly 20, automatically positioning the chambers 16, 24 without need for clips. The entire set now has a more comprehensible aspect to it, and the remaining set up becomes much easier, even for a novice.

First bubble trap chamber 16 is similar to that disclosed in the previously cited Schnell and Utterberg U.S. Ser. No. 08/905,245. As shown in FIG. 6, first bubble trap chamber 16 has a bottom inlet or first port tube 36 which enters the interior 38 of chamber 16, and receives blood from tube 14. Blood flow is deflected horizontally to the left by angled baffle wall 40. Blood flow within chamber interior 38 is then largely horizontal, going from the left end of chamber interior 38 (as in FIG. 6) to the right end, where an outlet flow path begins underneath horizontal wall 42. As shown, the outlet flow path passes under horizontal wall 42 and upwardly through second port tube 44 and out of the chamber into pump tubing 18. The substantially horizontal flow of blood within the chamber facilitates the collection of microbubbles at the top of the chamber, so that the blood which is flowing under horizontal wall 42 and out tube 44 is essentially bubble free. Angled wall 40 and horizontal wall 42 each extend from one sidewall 43 to the other of chamber 16, so that essentially all of the flow is substantially in the direction of the respective arrows shown in FIG. 6.

Bottom members 46 are dummy connectors of the shape of male luer lock connectors, serving as a site to which tubing terminated with a female luer lock connector can be secured in sterile, protected manner until needed for use. Male luer projection 46 may be solid, or at least closed off at its outer end, so that there can be no fluid flow therethrough.

Second bubble trap chamber 24 is of a novel design, being made in this embodiment of a generally cup-shaped main body 48 (FIG. 2) and a lid 50 in a manner where molding of second chamber 24 is simplified. The cup-shaped chamber portion 48 has a sidewall that defines a flow-diverting indentation 52, which is positioned between the ends of chamber 24. Correspondingly, indentation 52 defines on its outer surface a corresponding recess 54 through which connector tube 56, integral with lid 50, can extend. Thus, an end of pump tube 18 can connect to aperture 58 of connector tubing 56 at the top end, while third length of tubing 26 can be secured in flow relationship to the bottom of connecter tube 56, to provide a by-pass flow conduit that does not communicate with the interior of chamber 24, but is externally secured to chamber 24 for securance of a section of the arterial blood flow path to the venous chamber 24, to provide an order and rationality to the usually-complex array of tubings of an arterial and venous set.

Also, because the arterial and venous set components are connected together, it is possible to install them simultaneously, with the main act of installation being accomplished by the placement of the pump tubing 18 and the two chambers 16, 24 into a peristaltic pump module 20 of a dialyzer machine 22. Despite the blood flow conduit extending by chamber 24, it has a substantially flat backside 57 as indicated in FIG. 3, and a substantially flat top 59 (without projecting entry ports), so that it can conveniently be installed in conventional dialysis hardware.

Optionally, tubing 56, which is integral with lid 50, may be bifurcated to provide a smaller, second branch tube 60 which, in turn, may communicate with flexible branch tubing 62, so that heparin, saline solution, or other medicaments may be introduced into the system, or the pressure may be monitored, through line 62.

Turning now to the flow of fluid within second chamber 24, after blood has passed through dialyzer 12 as shown in FIG. 8, it flows through flexible length of tubing 32 into inlet tube 64, which is positioned on one side of chamber 24. Inlet tube 64 terminates in an upper wall 66 above an open side aperture 68, which causes fluid flow to pass horizontally into chamber 24 on one side of flow diverting indentation 52 defined in the wall of chamber 24. As particularly shown in FIG. 2, tube 64 may be defined as an integral part of lid 50, with the tube and its interior wall 66 being molded by appropriate core pins with lid 50. Thus, flow inlet tube 64 defines an open aperture 70 at the main horizontal surface of lid 50, but the presence of wall 66 in the middle of tube 64 prevents blood flow from proceeding vertically above wall 66, so that it all flows horizontally through aperture 68 in a horizontal flow that preferably has an initial height of typically less than half of the height of chamber 24.

Also, external connector tube 56, which connects with pump tubing 18 and length of flexible tubing 26 respectively at each end, may also be integrally molded with lid 50.

Accordingly, as particularly shown by FIG. 5, a main flow of blood within chamber 24 passes horizontally out of flow inlet tube 64 as indicated by flow path 72. The presence of flow diverting indentation 52 in the chamber wall helps to cause the majority of the blood flow from inlet tube 64 to flow initially horizontally in a direction that is substantially away from flow outlet 74 of chamber 24, which is positioned in the bottom wall 75 thereof (FIG. 7). Also to this end, side aperture 68 in flow inlet tube 64 is positioned to face at least about 90° away from the direction of flow outlet 74. Thus, the main, horizontal path of blood flow first extends rearwardly, then curving around as shown in FIG. 5 through an end area of chamber 24 which is more remote from flow outlet 74 than is flow inlet tube 64. Other flow is suppressed by indentation 52. Then, the general flow turns horizontally toward the other end of chamber 24 where flow outlet 74 resides, and proceeds to the flow outlet 74.

Thus, an increased amount of horizontal flow is provided in chamber 24 than would normally be provided in prior art chambers of similar size. This added degree of horizontal flow provides more opportunity for bubbles in the blood to migrate toward the top of chamber 24, to rest underneath lid 50 as the blood is withdrawn from the chamber through outlet port 74 downwardly from the bottom of the chamber. Thus, bubbles are not captured and caught in the outflow current as easily as in other designs of similar size and at similar flow rates.

A depth filter 76 is provided in at least a top portion of outlet port 74 for the usual blood filtration that is typically required in a venous set prior to returning blood to the patient.

The blood passes from outlet port 74 into a length of flexible tubing 34, and from there is returned through the patient by means of a typical fistula needle 13, which communicates with a fistula, a venous catheter, or the like.

A resealable injection site 78 may be carried in perpendicular manner on outlet port 74 for the addition of medicaments, parenteral solutions, or for the taking of samples as may be desired.

Also, venous chamber 24 comprises a side chamber 80 having a two level floor 82, 84, with each of the floor levels being substantially above the bottom wall 75 of the chamber. This side chamber with its two level floor carries a pair of apertures as shown, each of which connects to a flexible branch tubing 86, 88. Chamber 80 can be used in the control of the liquid level of chamber 24 during priming with solution and then also during use when blood is passing through the system. The floor of chamber portion 84 can serve as a liquid level restricter in the chamber during priming. If tubing 88 is open and unclamped, excess liquid in the chamber above the level of floor 84 can run out of tube 88, thus controlling the liquid level during priming. Then, during operation with tube 88 clamped off, tube 86 extending through floor 82 can be used to control the blood level in the chamber by adding or withdrawing air.

A dummy luer site 90 is found on the bottom of chamber 24, and may be used to secure a female luer connector or a luer lock connector on the end of one of the branch tubings under aseptic, out-of-the way conditions until the female luer is needed for connection elsewhere. As with dummy luer connectors 46, connector 90 has no port that communicates with the interior of chamber 24, but simply serves as a storage connector site for a female luer connector.

Referring to FIG. 4, an alternative design of flow inlet port tube 64*a* is provided. Here, the tube is a free standing structure which only extends partway through the height of chamber 24. Port tube 64*a* has a closed upper end and a side aperture 68*a*, which is similar in function to aperture 68 of the previous embodiment, being positioned as before to provide a circuitous, indirect blood flow path for most of the blood that initially moves away from the outlet port of the chamber.

Thus, a combined arterial-venous tubular set for the conveyance of blood to and from an extracorporeal blood treatment device is provided, which set carries novel bubble trap chambers, each of which exhibit improved bubble removing capability when compared with other chambers of comparable size and at comparable flow rates, because of the elongated horizontal flow path that is provided to blood within the respective chambers.

The above is offered for illustrative purposes only, and is not intended to be limited to the specific disclosures of this application, but is as defined in the claims below.

That which is claimed:

1. A combined arterial-venous blood flow set which comprises: connected lengths of flexible tubing for receiving blood from a patient, for conveying the blood to a blood processing device, and for returning the blood to the patient;

a first bubble trap chamber connected in series flow between two of said lengths of tubing at a flow position downstream from the patient and upstream from the blood processing device;

a second bubble trap chamber connected in series flow between two of said lengths of tubing at a flow position downstream from the blood processing device and upstream from the patient;

a first portion of said tubing in a flow position upstream from the blood processing device extending by said second bubble trap chamber and being physically connected thereto without direct flow connection, to help stabilize the positioning of components of said flow set.

2. The blood flow set of claim 1 in which one of said lengths of tubing comprises peristaltic pump tubing, said first bubble trap chamber being directly connected in flow communication to an end of said pump tubing, said second bubble trap chamber being connected to tubing connected and adjacent to said pump tubing but out of direct flow communication therewith.

3. The blood flow set of claim 1 in which said second bubble trap chamber comprises a chamber-defining housing, a flow inlet tube connected to a length of said flexible tubing which is in a flow portion downstream from the blood processing device, said flow inlet tube extending into said chamber adjacent one side of said chamber and having an aperture that directs substantially the entire blood flow through said inlet tube horizontally into said chamber, said housing having an outlet port adjacent to the chamber bottom and positioned adjacent a side of said chamber opposed to said one side; said chamber having a sidewall that defines a flow-diverting indentation positioned between said one side and said opposed side of the chamber, to interfere with a direct flow path for blood flowing through said chamber between said flow inlet tube and said outlet port.

4. The blood flow set of claim 3 in which said aperture of the flow inlet tube faces away from said outlet port by at least about 90°.

5. The blood flow set of claim 3 in which said first portion of tubing is connected to said second bubble trap chamber at a position adjacent to said indentation to permit fluid flow of said first portion of tubing to pass through a recess defined by the outside surface of a portion of the sidewall that defines said indentation, whereby the recess-defining side of said bubble trap chamber can stably rest against a flat surface during use, while providing an external blood flow passageway adjacent to said side.

6. The blood flow set of claim 5 in which the housing of said second bubble trap chamber defines an integral tube extending through said recess, said integral tube having opposed ends connected to separate lengths of said flexible tubing, to define said first portion of said tubing.

7. The blood flow set of claim 6 in which said housing of the second bubble trap chamber defines a cup-like main body defining a bottom wall and said sidewall, and a fitting lid which is sealed to said main body to define a closed chamber, said lid also defining said integral tube.

8. The blood flow set of claim 3 in which said sidewall defines at least one side chamber that is vertically spaced from the bottom of said bubble trap chamber, said side chamber having a port that connects to tubing located externally of said second bubble trap chamber.

9. The blood flow set of claim 3 in which a blood filter is carried in or adjacent to said outlet port, to filter blood passing through said outlet port.

10. The blood flow set of claim 1 in which said first bubble trap chamber has a flow inlet that directs flowing blood horizontally into said first chamber.

11. The blood flow set of claim 10 in which said first bubble trap chamber comprises:

a chamber having top, bottom, and side walls;

a first port tube communicating upwardly into said chamber;

a second port tube communicating downwardly into said chamber;

a flow-directing system positioned to direct incoming fluid from one of said port tubes into a first lateral flow direction, and then to allow substantially horizontal fluid flow circulation in said chamber, said flow-directing system also allowing fluid flow from circulating fluid in said chamber into the other of said port tubes in a lateral flow direction that is generally the same as said first lateral flow direction, while preventing direct flow between said first and second port tubes.

12. A blood flow set comprising connected lengths of flexible tubing for conveying blood between a patient and a blood processing device, and a bubble trap chamber connected in series flow between two lengths of said flexible tubing, said set also comprising added set tubing positioned to extend by said bubble trap chamber and being physically laterally connected thereto without direct flow connection, to help stabilize the positioning of components of said blood flow set.

* * * * *